US008668495B2

(12) United States Patent
Sanchez et al.

(10) Patent No.: US 8,668,495 B2
(45) Date of Patent: *Mar. 11, 2014

(54) CERAMIC/METALLIC DENTAL ABUTMENT

(71) Applicant: Zimmer Dental, Inc., Carlsbad, CA (US)

(72) Inventors: Ramiro Sanchez, Temecula, CA (US); Christopher M Gervais, San Marcos, CA (US); Jeffrey Bassett, Vista, CA (US)

(73) Assignee: Zimmer, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/850,569

(22) Filed: Mar. 26, 2013

(65) Prior Publication Data

US 2013/0209957 A1 Aug. 15, 2013

Related U.S. Application Data

(63) Continuation of application No. 13/425,706, filed on Mar. 21, 2012, now Pat. No. 8,439,680, which is a continuation of application No. 12/853,792, filed on Aug. 10, 2010, now Pat. No. 8,142,191, which is a continuation of application No. 11/362,236, filed on Feb. 24, 2006, now Pat. No. 7,780,446.

(51) Int. Cl.
*A61C 8/00* (2006.01)

(52) U.S. Cl.
USPC .......................................................... 433/173

(58) Field of Classification Search
USPC ........... 433/172–176, 201.1, 202.1, 215, 220, 433/221
See application file for complete search history.

(56) References Cited

U.S. PATENT DOCUMENTS

| 786,966 A | 4/1905 | Hennessy et al. |
| 1,124,501 A | 1/1915 | Monroe |

(Continued)

FOREIGN PATENT DOCUMENTS

| AT | 363869 B | 9/1981 |
| AT | 329546 T | 7/2006 |

(Continued)

OTHER PUBLICATIONS

"U.S. Appl. No. 13/425,706, Response filed Nov. 27, 2012 to Non Final Office Action mailed Oct. 1, 2012", 8 pgs.

(Continued)

*Primary Examiner* — Heidi M Eide
(74) *Attorney, Agent, or Firm* — Schwegman, Lundberg & Woessner, P.A.

(57) ABSTRACT

A ceramic and metallic dental abutment for use with a dental implant is disclosed. The abutment can generally include a body having a base region, a coronal region, and a transgingival region disposed between the base and coronal regions. The body regions can define a longitudinal axis. The base region can include an anti-rotational feature such that, when engaged with the dental implant, an anti-rotational connection exists. The coronal and transgingival regions can include a ceramic exterior surface. The abutment can further include a metal contact portion having an annular shape and positioned to engage the dental implant. The metal contact portion can include a conical outer contact surface, disposed at an oblique angle with respect to the longitudinal axis, to match an angle of a chamfer of the dental implant.

20 Claims, 4 Drawing Sheets

(56) References Cited

U.S. PATENT DOCUMENTS

| | | | |
|---|---|---|---|
| 1,269,932 A | | 6/1918 | Hix |
| 1,808,200 A | | 6/1931 | Bartram et al. |
| 2,263,155 A | | 11/1941 | Wright |
| 3,494,656 A | | 2/1970 | Mcintire |
| 3,636,195 A | | 1/1972 | Monson |
| 4,230,009 A | | 10/1980 | Coburn |
| 4,872,839 A | | 10/1989 | Brajnovic |
| 5,030,095 A | | 7/1991 | Niznick |
| 5,125,839 A | | 6/1992 | Ingber et al. |
| 5,152,687 A | | 10/1992 | Amino |
| 5,269,149 A | | 12/1993 | Zeidler |
| 5,281,140 A | | 1/1994 | Niznick |
| 5,336,090 A | | 8/1994 | Wilson et al. |
| 5,447,434 A | | 9/1995 | Shaw |
| 5,447,435 A | | 9/1995 | Brodbeck |
| 5,571,016 A | | 11/1996 | Ingber et al. |
| 5,685,714 A | | 11/1997 | Beaty et al. |
| 5,829,977 A | | 11/1998 | Rogers et al. |
| 5,947,732 A | | 9/1999 | Beaty et al. |
| 5,989,026 A | | 11/1999 | Rogers et al. |
| 6,012,923 A | * | 1/2000 | Bassett et al. ............ 433/172 |
| 6,152,737 A | | 11/2000 | Beaty et al. |
| 6,168,435 B1 | | 1/2001 | Beaty et al. |
| RE37,227 E | | 6/2001 | Brodbeck |
| 6,343,930 B1 | | 2/2002 | Beaty et al. |
| 6,878,456 B2 | * | 4/2005 | Castro et al. ............ 433/229 |
| 7,445,396 B2 | | 11/2008 | Cheng |
| 7,780,446 B2 | | 8/2010 | Sanchez et al. |
| 8,142,191 B2 | | 3/2012 | Sanchez et al. |
| 8,439,680 B2 | | 5/2013 | Sanchez et al. |
| 2004/0101807 A1 | | 5/2004 | Porter et al. |
| 2004/0185417 A1 | | 9/2004 | Rassoli |
| 2004/0197737 A1 | * | 10/2004 | Uckelmann et al. ........ 433/173 |
| 2004/0234926 A1 | | 11/2004 | Halldin |
| 2005/0014108 A1 | | 1/2005 | Wohrle et al. |
| 2005/0084819 A1 | * | 4/2005 | Sims et al. ............ 433/173 |
| 2005/0136378 A1 | | 6/2005 | Ennajimi et al. |
| 2005/0244789 A1 | * | 11/2005 | Crohin et al. ............ 433/173 |
| 2006/0099549 A1 | * | 5/2006 | Engman ............ 433/173 |
| 2006/0105296 A1 | | 5/2006 | Linder et al. |
| 2006/0286509 A1 | * | 12/2006 | Bassett et al. ............ 433/173 |
| 2012/0178047 A1 | | 7/2012 | Sanchez et al. |

FOREIGN PATENT DOCUMENTS

| | | |
|---|---|---|
| AT | 363869 A | 6/2007 |
| AU | 3636195 A | 4/1997 |
| AU | 7445396 A | 5/1997 |
| AU | 1808200 A | 5/2000 |
| AU | 2007220957 B2 | 9/2012 |
| BR | 9914404 A | 10/2001 |
| DE | 4230009 A1 | 10/1995 |
| DE | 20110768 U1 | 11/2002 |
| DE | 69534973 T2 | 9/2006 |
| EP | 0786966 A1 | 8/1997 |
| EP | 1124501 A1 | 8/2001 |
| EP | 1269932 A1 | 1/2003 |
| EP | 1993469 | 11/2008 |
| ES | 2263155 T3 | 12/2006 |
| JP | 1050937 A | 2/1989 |
| JP | 5269149 A | 10/1993 |
| JP | 10509371 A | 9/1998 |
| JP | 11506688 A | 6/1999 |
| JP | 2002528169 A | 9/2002 |
| JP | 3494656 B2 | 2/2004 |
| JP | 2009527339 A | 7/2009 |
| JP | 5017285 | 6/2012 |
| TW | 442272 B | 6/2001 |
| WO | WO-9710770 A1 | 3/1997 |
| WO | WO9714372 | 4/1997 |
| WO | WO-9714372 A1 | 4/1997 |
| WO | WO-0024335 A1 | 5/2000 |
| WO | WO-2006012273 A1 | 2/2006 |

OTHER PUBLICATIONS

"Canadian Application Serial No. 2,643,036, Office Action mailed Apr. 22, 2013", 3 pgs.

"U.S. Appl. No. 11/362,236, Decision on Pre-Appeal Brief Request mailed May 5, 2008", 2 pgs.

"U.S. Appl. No. 11/362,236, Final Office Action mailed Feb. 9, 2009", 9 pgs.

"U.S. Appl. No. 11/362,236, Final Office Action mailed Aug. 10, 2007", 8 pgs.

"U.S. Appl. No. 11/362,236, Final Office Action mailed Nov. 15, 2007", 9 pgs.

"U.S. Appl. No. 11/362,236, Final Office Action mailed Dec. 11, 2006", 7 pgs.

"U.S. Appl. No. 11/362,236, Non Final Office Action mailed Mar. 5, 2007", 8 pgs.

"U.S. Appl. No. 11/362,236, Non Final Office Action mailed Jul. 5, 2006", 9 pgs.

"U.S. Appl. No. 11/362,236, Non Final Office Action mailed Aug. 27, 2008", 7 pgs.

"U.S. Appl. No. 11/362,236, Non Final Office Action mailed Sep. 14, 2009", 10 pgs.

"U.S. Appl. No. 11/362,236, Notice of Allowance mailed Apr. 19, 2010", 6 pgs.

"U.S. Appl. No. 11/362,236, Pre Appeal Brief Request filed Mar. 28, 2008", 8 pgs.

"U.S. Appl. No. 11/362,236, Response filed Jan. 18, 2007 to Final Office Action mailed Dec. 11, 2006", 10 pgs.

"U.S. Appl. No. 11/362,236, Response filed Jan. 22, 2010 to Non Final Office Action mailed Sep. 14, 2009", 11 pgs.

"U.S. Appl. No. 11/362,236, Response filed Feb. 6, 2007 to Final Office Action mailed Dec. 11, 2006", 9 pgs.

"U.S. Appl. No. 11/362,236, Response filed May 25, 2007 to Non Final Office Action mailed Mar. 5, 2007", 10 pgs.

"U.S. Appl. No. 11/362,236, Response filed Jun. 5, 2008 to Final Office Action mailed Nov. 15, 2007", 12 pgs.

"U.S. Appl. No. 11/362,236, Response filed Jul. 9, 2009 to Final Office Action mailed Feb. 9, 2009", 19 pgs.

"U.S. Appl. No. 11/362,236, Response filed Oct. 3, 2006 to Non Final Office Action mailed Jul. 5, 2006", 9 pgs.

"U.S. Appl. No. 11/362,236, Response filed Oct. 26, 2007 to Final Office Action mailed Aug. 10, 2007", 10 pgs.

"U.S. Appl. No. 11/362,236, Response filed Nov. 12, 2008 to Non Final Office Action mailed Aug. 27, 2008", 13 pgs.

"U.S. Appl. No. 12/853,792, Non Final Office Action mailed Jul. 14, 2011", 11 pgs.

"U.S. Appl. No. 12/853,792, Notice of Allowance mailed Jan. 26, 2012", 9 pgs.

"U.S. Appl. No. 12/853,792, Response filed Dec. 14, 2011 to Non Final Office Action mailed Jul. 14, 2011", 9 pgs.

"U.S. Appl. No. 13/425,706, Response filed Aug. 22, 2012 to Non Final Office Action mailed May 30, 2012", 11 pgs.

"U.S. Appl. No. 13/425,706, Non Final Office Action mailed May 30, 2012", 10 pgs.

"U.S. Appl. No. 13/425,706, Non Final Office Action mailed Oct. 1, 2012", 4 pgs.

"U.S. Appl. No. 13/425,706, Notice of Allowance mailed Jan. 16, 2013", 5 pgs.

"Australian Application Serial No. 2007220957, First Examiners Report mailed Nov. 7, 2011", 1 pg.

"Australian Application Serial No. 2007220957, Office Action Response File May 29, 2012", 2 pgs.

"European Application Serial No. 07756752.7, Office Action mailed Oct. 22, 2008", 2 pgs.

"European Application Serial No. 07756752.7, Response filed Dec. 1, 2008 to Office Action mailed Oct. 22, 2008", 8 pgs.

"International Application Serial No. PCT/US1999/024886, International Search Report mailed Apr. 14, 2000", 2 pgs.

"International Application Serial No. PCT/US2007/016819, International Search Report mailed Mar. 21, 2008", 3 pgs.

"International Application Serial No. PCT/US2007/016819, International Search Report mailed Jul. 24, 2007", 2 pgs.

(56) References Cited

OTHER PUBLICATIONS

"International Application Serial No. PCT/US2007/061819, International Preliminary Report on Patentability mailed Aug. 26, 2008", 6 pgs.

"International Application Serial No. PCT/US2007/061819, International Search Report mailed Jul. 24, 2007", 2 pgs.

"International Application Serial No. PCT/US2007/061819, Written Opinion mailed Jul. 24, 2007", 5 pgs.

"International Application Serial No. PCT/US2007/202463, Examination Reports dated Jul. 5, 2007", 3 pgs.

"Japanese Application Serial No. 2008-556493, Office Action mailed Feb. 28, 2012", (w/ English Translation), 4 pgs.

"Japanese Application Serial No. 2008-556493, Response filed May 14, 2012 to Office Action mailed Fefb. 28, 2012", (w/ English Translation), 5 pgs.

\* cited by examiner

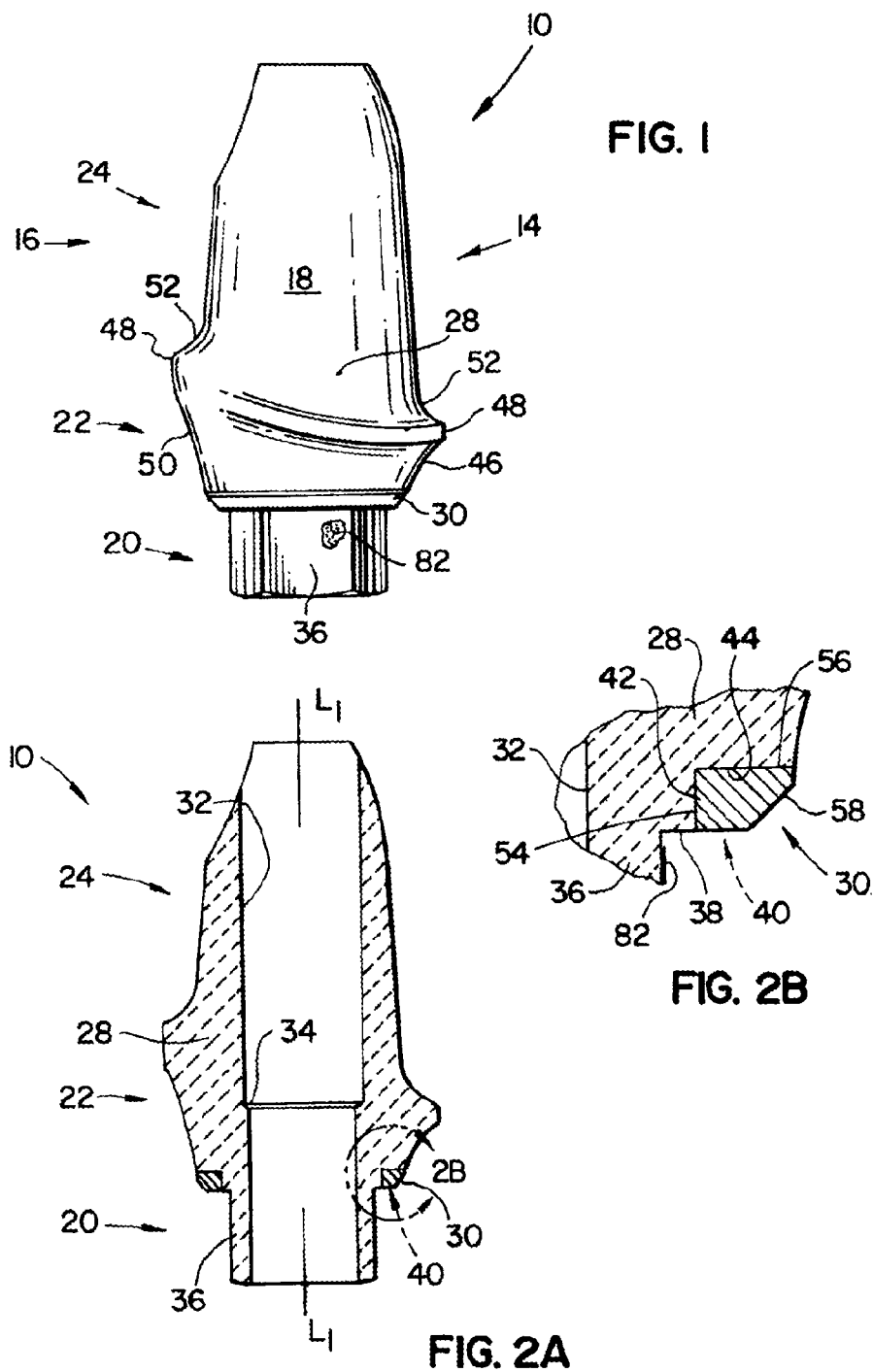

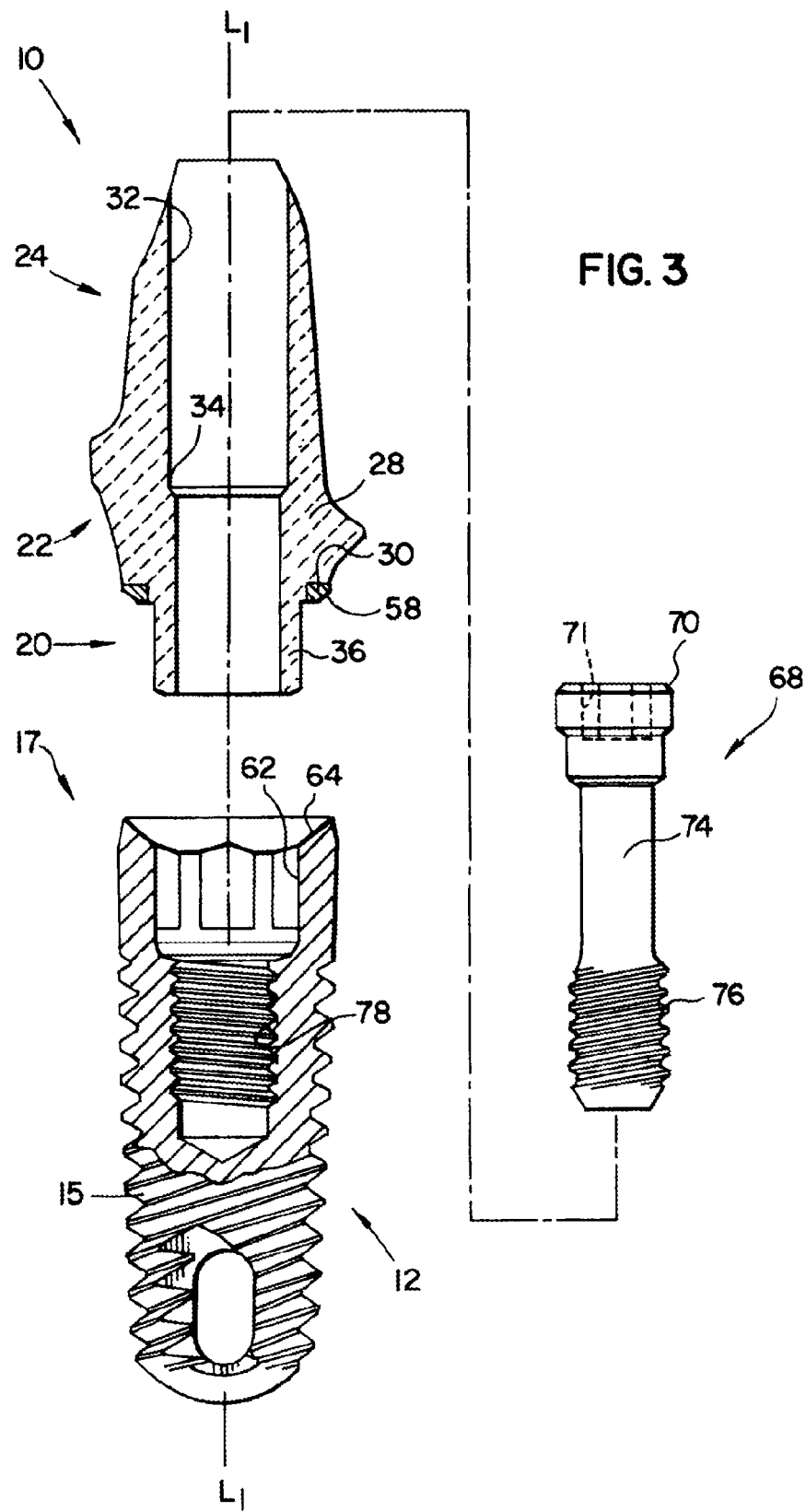

CERAMIC/METALLIC DENTAL ABUTMENT

CROSS-REFERENCE TO RELATED APPLICATIONS

This application is a continuation of U.S. patent application Ser. No. 13/425,706, filed Mar. 21, 2012, and issued as U.S. Pat. No. 8,439,680 on May 14, 2013; which is a continuation of U.S. patent application Ser. No. 12/853,792, filed Aug. 10, 2010 and issued as U.S. Pat. No. 8,142,191 on Mar. 27, 2012; which is a continuation of U.S. patent application Ser. No. 11/362,236, filed Feb. 24, 2006 and issued as U.S. Pat. No. 7,780,446 on Aug. 24, 2010, each of which is incorporated herein in its entirety for all purposes.

FIELD OF THE INVENTION

The present invention relates to dental prosthetics and, in particular, to a ceramic/metallic abutment for use with a dental implant as part of a prosthodontic restoration.

DESCRIPTION OF THE RELATED ART

Dental implants are commonly used as anchoring members in prosthodontic restorations to provide prosthetic teeth at one or more edentulous sites in a patient's dentition at which the patient's original natural teeth have been lost or damaged. Typically, known implant systems include a dental implant made from a suitable biocompatible material, such as titanium. The dental implant is typically threaded into a bore which is drilled into the patient's mandible or maxilla at the edentulous site. The implant provides an anchoring member for a dental abutment, which in turn provides an interface between the implant and a dental restoration. The restoration is typically a porcelain crown fashioned according to known methods to replicate the shape of the tooth being replaced.

Many current dental implant surgeries are performed in two stages. In the initial or first stage, an incision is made in the patient's gingiva at an edentulous side, and a bore is drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's jaw bone grows around the implant to securely anchor the implant in the surrounding bone, a process known as osseointegration.

In a second stage of the procedure following osseointegration, the dentist surgically reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. In the final stage, the temporary prosthesis or healing member is removed and replaced with the permanent prosthesis, which is attached to the abutment with cement or with a fastener, for example.

Typically, abutments are made from a biocompatible metal, such as titanium, or from a ceramic material. Advantages of titanium abutments include structural strength and relative ease of manufacture. However, if recession of the gingival tissue occurs around the implant and abutment after implantation, there is the potential that a portion of the metal of the abutment beneath the crown may become exposed, such that the grey color of the titanium is visible, which is aesthetically disadvantageous.

Ceramic abutments are harder than titanium abutments, and have the additional advantage of providing a light, tooth-like color such that, in the event of gingival recession, the light color of any exposed portions of the abutment substantially match the color of the crown and appear tooth-like to preserve aesthetics.

What is needed is an abutment which is an improvement over the foregoing.

SUMMARY OF THE INVENTION

The present invention provides a ceramic/metallic dental abutment for use with an implant, the abutment generally including a ceramic body portion having a base region, a transgingival region, and a supragingival region. The base region includes an anti-rotational implant interface, such as an external polygonal fitting, for engaging a cooperating internal polygonal fitting of an implant to prevent relative rotation between the abutment and the implant. The ceramic abutment body portion additionally includes a metal implant contact portion for contacting the implant and providing a load-bearing, metal-on-metal interface between the abutment and the implant.

In one embodiment, the implant contact portion is provided in the form of an annular metal ring made of titanium, for example, which is attached to the abutment via a press-fit connection, an adhesive connection, a shrink-fit connection, a brazed connection, or in another suitable manner. The implant contact portion is disposed substantially at the interface between the base region and the transgingival region of the abutment, and is dimensioned such that, when the abutment is connected to the implant, the implant contact portion is substantially entirely contained within the outer periphery of the open proximal end of the implant. Therefore, after attachment of the abutment to the implant, the implant contact portion is not visible and does not contact soft tissue surrounding the abutment.

In one embodiment, the proximal end of the implant includes an annular chamfer disposed at an oblique angle with respect to the longitudinal axis of the implant and abutment, and the implant contact portion of the abutment includes a contact surface disposed at a cooperating angle for engagement with the implant chamfer. The internal polygonal fitting of the implant may be greater in length than the external polygonal fitting of the abutment such that, upon receipt of the external polygonal abutment fitting into the internal polygonal implant fitting, relative rotation between the abutment and implant is prevented while axial loads from the abutment, such as occlusal and/or mastication loads, for example, are transferred to the implant only through the implant contact portion for improved resistance to wear.

In one form thereof the present invention provides a dental abutment, including a ceramic body portion defining a longitudinal axis, and including a base region with an anti-rotational implant interface, a transgingival region, and a supragingival region; a bore extending through the body portion along the longitudinal axis; and a metal implant contact portion attached to the body portion and disposed adjacent the implant interface.

In another form thereof, the present invention provides a dental abutment, including a ceramic body portion having a longitudinal axis, a bore extending through the body portion along the longitudinal axis, and an anti-rotational implant interface; and metal implant contact means attached to the body portion for axial load-bearing contact with an implant.

In a further form thereof, the present invention provides, in combination, a dental implant, including an externally threaded body having a distal end and a proximal end; a bore extending into the proximal end, the bore including a threaded portion and a first anti-rotational interface; and a dental abutment, including a ceramic body portion including a second anti-rotational interface cooperable with the first anti-rotational interface of the implant whereby relative rotation between the abutment and the implant is prevented; and a metal contact portion abuttable with the proximal end of the implant.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1 is a perspective, interproximal view of a ceramic/metallic abutment in accordance with the present invention;

FIG. 2A is a sectional view of the abutment of FIG. 1;

FIG. 2B is a fragmentary view of a portion of FIG. 2A;

FIG. 3 is a sectional, exploded view showing the abutment together with an implant and an abutment screw;

Corresponding reference characters indicate corresponding parts throughout the several views. The exemplifications set out herein illustrate preferred embodiments of the invention, and such exemplifications are not to be construed as limiting the scope of the invention any manner.

DETAILED DESCRIPTION

Figure 4:
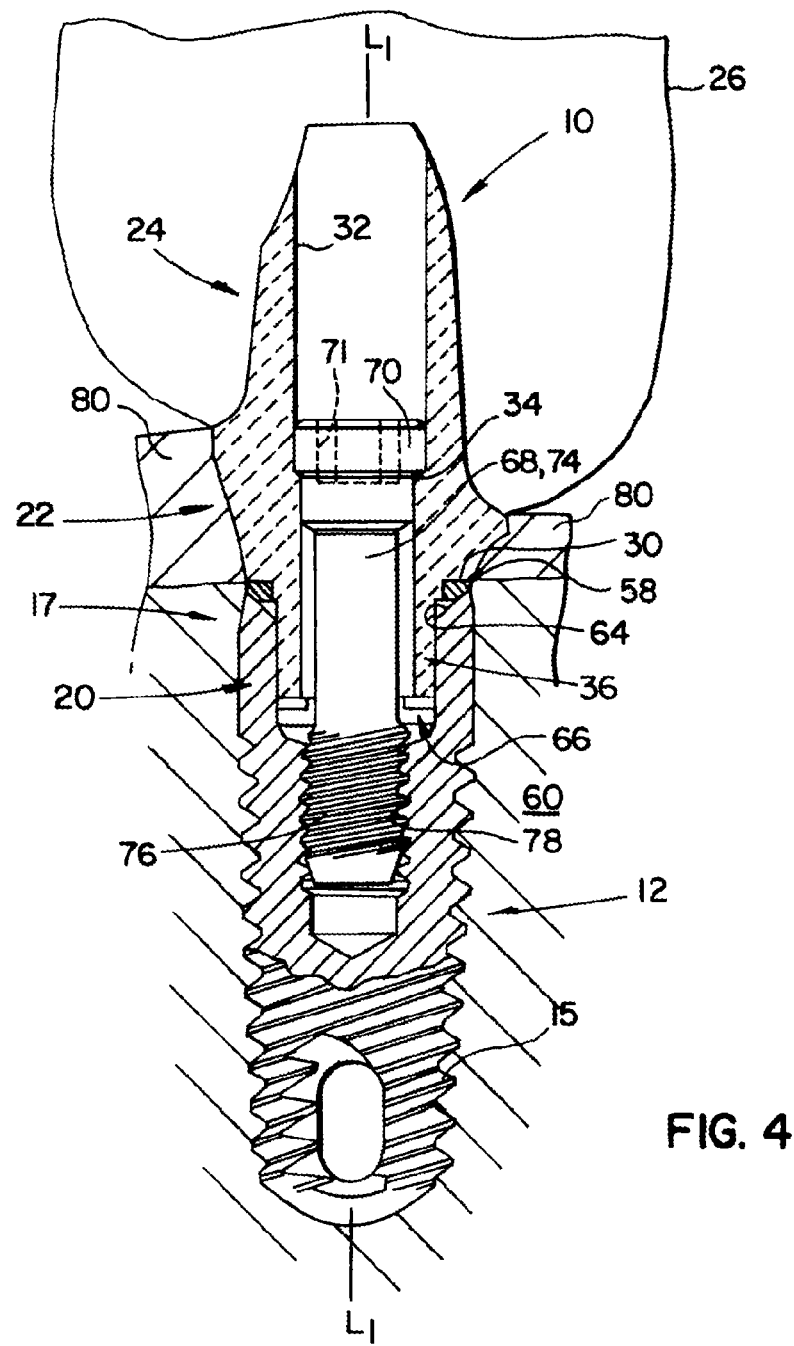
FIG. 4 is a sectional view of the implant, abutment, and abutment screw of FIG. 3, with the implant implanted within a jawbone and a crown secured to the abutment.

Referring first to FIGS. 1, 2A, and 2B, a ceramic/metallic dental abutment 10 according to the present invention is shown, which may be used with a dental implant 12, such as that shown in FIGS. 3 and 4 and described below, to provide a prosthetic tooth at an edentulous site in a patient's dentition at which a natural tooth has been lost or damaged. In FIG. 1, an interproximal view of abutment 10 is shown, which includes a facial side 14 and an opposing lingual side 16, as well as a mesial side 18 and an opposing distal side (not visible in FIG. 1). Abutment 10 also generally includes a base region 20 for interfacing with implant 12, an emergence profile region or transgingival region 22 which extends through soft gingival tissue, and a coronal region or supragingival region 24 extending superiorly of transgingival region 22 to which a prosthetic tooth or crown 26 may be attached, as shown in FIG. 4.

Abutment 10 includes a body portion 28 made of a suitable ceramic material, such as aluminum oxide or zirconium oxide, for example, and body portion 28 additionally includes an implant contact portion 30, described below, which may be made of a suitable biocompatible metal, such as titanium, for example. As shown in FIG. 2A, body portion 28 of abutment 10 includes a central bore 32 therethrough extending along the longitudinal axis $L_1$-$L_1$ of abutment 10, with bore 32 including step 34 for abutting engagement by the head of an abutment screw to secure abutment 10 to implant 12 in the manner described below. Although transgingival region 22 and supragingival region 24 of abutment 10 extend substantially along the direction of longitudinal axis $L_1$-$L_1$ in the embodiment shown in FIGS. 1-4, in other embodiments, transgingival region 22 and/or supragingival region 24 of abutment 10 may be angled away from bore 32 and longitudinal axis $L_1$-$L_1$ as needed to conform to the anatomical orientation of the tooth being replaced.

Figure 5:
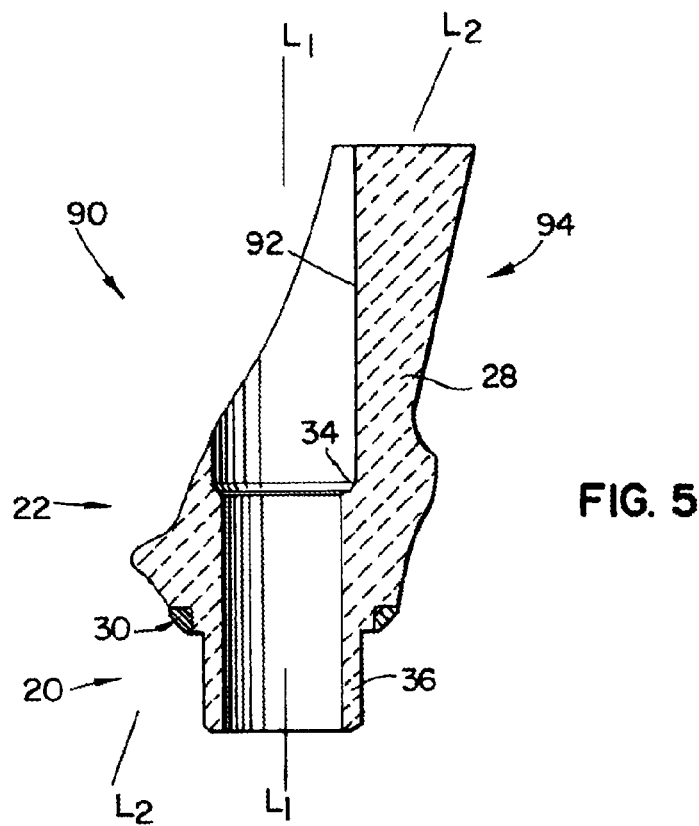
FIG. 5 is a sectional view of an angled abutment according to a further embodiment.

For example, referring to FIG. 5, an angled abutment 90 is shown which, except as described below, is substantially identical to abutment 10, and the same reference numerals are used to designate identical features therebetween. In abutment 90, central bore 92 thereof is disposed along central longitudinal axis $L_1$-$L_1$ of abutment 90, while supragingival region 94 of abutment 90 is oriented or disposed along an axis $L_2$-$L_2$ which angled with respect to central bore 94 and longitudinal axis $L_1$-$L_1$.

Base region 20 of abutment 10 includes an implant interface, shown herein as an external polygonal fitting 36 having a hexagonal shape. In other embodiments, abutment 10 could include an internal polygonal fitting and/or a polygonal fitting which includes more or less than six sides. Referring additionally to FIG. 2B, at its upper end adjacent transgingival region 22, polygonal fitting 36 terminates at shelf 38 adjacent a notch 40 disposed substantially at the transition of base region 20 and transgingival region 22, with notch 40 including annular rim 42 and annular base wall 44 within which implant contact portion 30 is fitted, as described below.

Referring to FIG. 1, transgingival region 22 of abutment 10 includes concave surface 46 extending toward margin shoulder 48 of transgingival region 22 on facial side 14 of abutment 10, and another concave surface 50 extending toward margin shoulder 48 on lingual side 16 of abutment 10. Margin shoulder 48 is disposed substantially at the gingival or gum line, is contoured to follow the gingival line based on the anatomy of the tooth being replaced, and includes concave recesses 52 on each of its sides which merge into the outer profile of supragingival region 24.

Referring to FIGS. 1, 2A, and 2B, abutment body portion 28 additionally includes an implant contact portion 30, shown herein in the form of an annular metal ring, for example. Implant contact portion 30 may be made of substantially the same material as implant 12, such as a suitable biocompatible metal, for example, titanium. As best shown in FIG. 2B, implant contact portion 30 generally includes annular inner surface 54 and annular top surface 56 disposed against rim 42 and base wall 44 of notch 40 of abutment body portion 28, respectively, as well as an implant contact surface 58 disposed at an oblique angle with respect to longitudinal axis $L_1$-$L_1$ of abutment 10, which surface contacts implant 12 in the manner described below.

Implant contact portion 30 may be attached to abutment body portion 28 via a press-fit connection, in which implant contact portion 30 is pressed with force onto rim 42 and against base wall 44 within notch 40 to firmly retain same on body portion 28 of abutment 10; an adhesive connection, in which a suitable adhesive or cement is applied between notch 40 and implant contact portion 30 which, when cured, firmly secures implant contact portion 30 to abutment body portion 28 within notch 40; a shrink-fit connection, in which implant contact portion 30 is heated, pressed onto rim 42 against base wall 44 within notch 40, and is then cooled to shrink the diameter of implant contact portion 30 slightly such that same is firmly retained to abutment body portion 28; or a brazed connection, in which implant contact portion 30 is pressed around rim 42 against base wall 44 within notch 40 and is then heat brazed to body portion 28.

Referring to FIGS. 3 and 4, implant 12 includes a threaded body 15 which is implanted into a tapped bore in the jawbone 60 (FIG. 4) of a patient according to known surgical techniques. After implant 12 is allowed to osseointegrate within jawbone 60, abutment 10 is initially seated on implant 12 by inserting external polygonal fitting 36 of abutment 10 into an internal polygonal fitting 62 of implant 12. Also, when abutment 10 is seated on implant 12, implant contact portion 30 of abutment 10 engages an internal annular chamfer 64 at the proximal end 17 of implant 12. Implant contact surface 58 of implant contact portion 30 of abutment 10 and chamfer 64 of implant 12 are complementary angled at an oblique angle relative to longitudinal axis $L_1$-$L_1$ of abutment 10 and implant 12.

As may be seen in FIG. 4, external polygonal fitting 36 of abutment 10 is slightly shorter along the direction of longitudinal axis $L_1$-$L_1$ of abutment 10 and implant 12 than internal polygonal fitting 60 of implant 12, such that an axial clearance space 66 is provided within internal polygonal fitting 62 of implant 12 distally of external polygonal fitting 36 of abutment 10. In this manner, the engagement between external polygonal fitting 36 of abutment 10 and internal polygonal fitting 60 of implant 12 prevents rotation of abutment 10 with respect to implant 12 without supporting the weight of abutment 10 and crown 26 or bearing loads along the direction of longitudinal axis $L_1$-$L_1$ of abutment 10. Rather, the metal-on-metal contact between implant contact portion 30 of abutment 10 and chamfer 64 of implant 12 supports the weight of abutment 10 and crown 26, as well as loads imposed upon abutment 10 and crown 26 along or divergent from the direction of longitudinal axis $L_1$-$L_1$ of abutment 10, such as occlusal and/or mastication loads, for example.

An abutment screw 68, shown in FIG. 3, is provided for securing abutment 10 to implant 12, and generally includes head 70 with instrument engagement structure such as an internal polygonal fitting 71, for example, as well as shank portion 74 extending from head 70 and having threads 76 thereon distally of head 70. In use, abutment screw 68 is inserted through central bore 32 of abutment 10, and threads 76 of abutment screw 68 are threaded into internally threaded region 78 of implant 12 with head 70 of abutment screw 68 initially seating against step 34 within internal bore 32 of abutment 10.

Thereafter, further tightening of abutment screw 68 presses head 70 thereof against seat 34 to firmly engage abutment 10 to implant 12 and, more specifically, to firmly press implant contact portion 30 of abutment 10 into engagement with chamfer 64 of implant 12, such that the loads imposed via abutment screw 68 along the direction of longitudinal axis $L_1$-$L_1$ of abutment 10 are transferred to implant 12 directly through implant contact portion 30. The firm engagement between implant contact portion 30 of abutment 10 and chamfer 64 of implant 12 minimizes micromotion between abutment 10 and implant 12.

After abutment screw 68 is tightened, abutment 10 is securely retained to implant 12 via the engagement of implant contact portion 30 of abutment 10 with chamfer 64 of implant 12, wherein a small gap may be present between external polygonal fitting 36 of abutment 10 and internal polygonal fitting 60 of implant 12 such that direct contact between the ceramic material of external polygonal fitting 36 of abutment 10 and the metal of internal polygonal fitting 60 of implant 12 is minimized. Advantageously, the metal-on-metal contact between implant contact portion 30 and implant 12 provides increased resistance to wear therebetween, due to the similarity or identity of the materials of implant contact portion 30 and implant 12.

After abutment 10 is secured to implant 12 in the manner described above, crown 26 may be attached to supragingival region 24 of abutment 10 via cement, for example, to complete the restoration. Advantageously, as can be seen in FIGS. 3 and 4, implant contact portion 30 of abutment 10 is disposed substantially entirely within the open proximal end 17 of implant 12 such that implant contact portion 30 is not visible externally of the prosthetic and, in the event of recession of gingival tissue 80 around transgingival region 22 of abutment 10, implant contact portion 30 will not be visible. Further, receipt of implant contact portion 30 substantially entirely within the open proximal end 17 of implant 12 as shown in FIG. 4 prevents the metal of implant contact portion 30 from contacting the soft gingival tissue 80 around abutment 10 and implant 12.

As shown in part in FIGS. 1 and 2B, ceramic body portion 28 and/or implant contact portion 20, in the area of base region 20 and/or transgingival region 22 of abutment 10, may be coated with a thin coating 82 of gold or other metallic or non-metallic coating, such as by electroplating or sputtering techniques, for example, such as for providing a light, tooth-like coloring for aesthetics.

Figure 6:
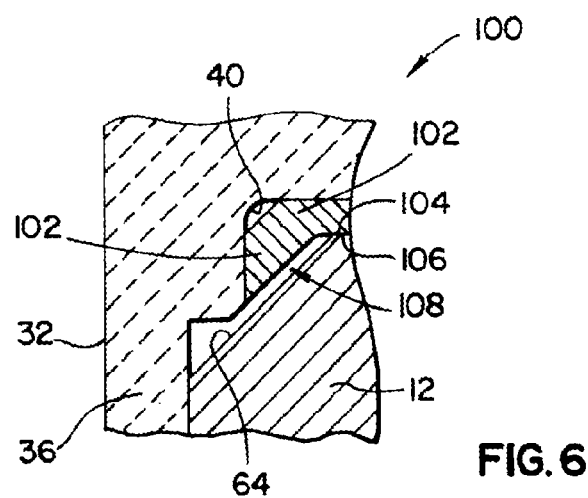
FIG. 6 is an enlarged fragmentary view of a portion of an abutment according to another embodiment.

Referring to FIG. 6, a portion of an abutment 100 according to another embodiment is shown which, except as described below, is identical to abutment 10 described above, and the same reference numerals are used to indicate identical or substantially identical features therebetween. Abutment 100 includes contact portion 102 similar to contact portion 30 described above, and which may be attached to abutment 100 in the same manner as contact portion 30 is attached to abutment 10. Contact portion 102 includes an annular outer end surface 104 dimensioned to seat on a proximal, outer annular rim 106 of implant 12, which a small clearance space 108 present between contact portion 102 and chamfer 64 of implant 12, wherein load are transferred from abutment 100 to implant 12 via outer end surface 104 of contact portion 102 to the proximal, outer annular rim 106 of implant 12.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A dental abutment configured for connection to a dental implant, comprising:
 a body having a base region, a coronal region, and a transgingival region disposed between the base and coronal regions, the body defining a longitudinal axis, the coronal and transgingival regions including a ceramic exterior surface;
 the base region including an anti-rotational feature such that, when engaged with the dental implant, an anti-rotational connection exists, wherein an external surface of the base region defines a notch having an annular shelf extending radially outwardly from the base region, an annular rim extending upwardly from the annular shelf, and an annular base wall extending radially outwardly from an upper end of the annular rim opposite the annular shelf;
 a central bore extending from a coronal end of the body to an apical end of the body;
 a screw seat positioned in the central bore between the coronal end and the apical end, and configured to engage a surface of a fastening screw, wherein the screw seat includes an inner diameter less than a diameter of the central bore at a location coronal to the screw seat; and a metal contact portion connected to the notch of the base region and configured to engage the dental implant, the metal contact portion having an annular shape and including a conical outer contact surface, disposed at an oblique angle with respect to the longitudinal axis, to match an angle of a chamfer of the dental implant.

2. The dental abutment of claim 1, wherein the metal contact portion includes an annular inner surface facing and engaging the annular rim, an annular top surface facing and engaging the annular base wall, and the conical outer contact surface.

3. The dental abutment of claim 1, wherein the transgingival region includes a margin shoulder configured to be positionable at a gum line and contoured to follow a gingival line of a tooth being replaced.

4. The dental abutment of claim 3, wherein the transgingival region includes a first concave surface extending from the annular base wall towards the margin shoulder on a lingual side.

5. The dental abutment of claim 4, wherein the transgingival region includes a second concave surface extending from the annular base wall towards the margin shoulder on a facial side.

6. The dental abutment of claim 1, wherein the anti-rotational feature includes a polygonal shape having at least three sides.

7. The dental abutment of claim 1, wherein the anti-rotational feature includes an external polygonal-shaped fitting.

8. The dental abutment of claim 1, wherein the metal contact portion is attached to a ceramic portion of the body in a manner selected from the group consisting of a press-fit connection, an adhesive connection, a shrink-fit connection, and a brazed connection.

9. The dental abutment of claim 1, wherein the transgingival region includes a center of mass defining an axis that is angled with respect to the longitudinal axis.

10. The dental abutment of claim 1, wherein the metal contact portion defines a through-bore, and wherein the base region extends within the through-bore.

11. The dental abutment of claim 1, wherein the metal contact portion includes an outer cylindrical surface portion contiguous with the ceramic exterior surface of the transgingival region.

12. The dental abutment of claim 1, wherein the metal contact portion is spaced from an apical end of the base region.

13. The dental abutment of claim 1, wherein a portion of the ceramic exterior surface is comprised of a coating providing a light color.

14. The dental abutment of claim 13, wherein the coating is comprised of a metallic substance.

15. The dental abutment of claim 13, wherein the coating is comprised of a non-metallic substance.

16. A dental device generally defining a longitudinal axis and comprising:

a dental implant having a coronal end including a coronal opening, with a chamfer surface extending at an oblique angle relative to the longitudinal axis, and a first anti-rotational interface, located distal to a distal end of the chamfer surface;

a dental abutment including a body, having a base region, a coronal region, and a transgingival region disposed between the base and coronal regions, and a metal contact portion, the base region including a second anti-rotational interface such that, when engaged with the first anti-rotational interface, an anti-rotational connection exists, wherein an external surface of the base region defines a notch having an annular rim extending upwardly from a point between an apical end of the base region and the transgingival region, and an annular base wall extending radially outwardly from an upper end of the annular rim, the coronal and transgingival regions including a ceramic exterior surface, the metal contact portion connected to the notch of the base region and configured to engage the dental implant, the metal contact portion having an annular shape and including a conical outer contact surface, disposed at an oblique angle with respect to the longitudinal axis, to match the angle of the chamfer of the dental implant; and a screw configured for connecting the dental implant to the dental abutment and for engaging a screw seating surface on the dental abutment.

17. The dental device of claim 16, wherein the first anti-rotational interface and the second anti-rotational interface each include a polygonal shape.

18. The dental device of claim 16, wherein the metal contact portion includes an annular inner surface facing and engaging the annular rim, an annular top surface facing and engaging the annular base wall, and the conical outer contact surface.

19. The dental device of claim 16, wherein the transgingival region includes a center of mass defining an axis that is angled with respect to the longitudinal axis.

20. The dental abutment of claim 16, wherein the connection of the metal contact portion to the notch of the base region includes at least one of a press-fit connection, an adhesive connection, a shrink-fit connection, and a brazed connection.

* * * * *